US006775642B2

(12) United States Patent
Remboski et al.

(10) Patent No.: US 6,775,642 B2
(45) Date of Patent: Aug. 10, 2004

(54) FAULT DETECTION SYSTEM HAVING AUDIO ANALYSIS AND METHOD OF USING THE SAME

(75) Inventors: Donald J. Remboski, Dearborn, MI (US); William F. Zancho, Hawthorn Woods, IL (US)

(73) Assignee: Motorola, Inc., Schaumburg, IL (US)

( * ) Notice: Subject to any disclaimer, the term of this patent is extended or adjusted under 35 U.S.C. 154(b) by 10 days.

(21) Appl. No.: 10/213,784

(22) Filed: Aug. 7, 2002

(65) Prior Publication Data

US 2003/0196492 A1 Oct. 23, 2003

Related U.S. Application Data

(60) Provisional application No. 60/373,156, filed on Apr. 17, 2002.

(51) Int. Cl.$^7$ .............................................. G06F 17/00
(52) U.S. Cl. ......................... 702/185; 702/183; 73/660
(58) Field of Search ............................... 702/182–185, 702/39, 33–36, 56, 66, 70, 71, 73–78, 113–115, 111, 122, 124, 126, 145, 188, 191, 193, 195, FOR 103, FOR 104, FOR 107, FOR 108, FOR 110, FOR 123, FOR 126, FOR 134, FOR 135, FOR 136, FOR 166, FOR 168, FOR 170, FOR 171; 73/593, 570, 579, 602, 646, 648, 659–661, 112, 116, 117.3; 701/29, 30, 34, 35, 33, 99; 324/613, 614; 381/58, 71.1, 71.4, 71.12, 86, 111–125, 355; 340/445, 679–683, 3.43, 438; 700/79, 80, 280

(56) References Cited

U.S. PATENT DOCUMENTS

| 4,083,234 A | | 4/1978 | Aono et al. .................... 73/116 |
|---|---|---|---|
| 4,988,979 A | * | 1/1991 | Sasaki et al. ................ 340/683 |
| 5,109,695 A | | 5/1992 | James et al. ................ 73/117.3 |
| 5,210,704 A | | 5/1993 | Husseiny |
| 5,278,760 A | | 1/1994 | Ribbens et al. ............. 701/111 |
| 5,387,253 A | | 2/1995 | Remboski, Jr. et al. .... 73/117.3 |
| 5,400,644 A | | 3/1995 | Remboski, Jr. et al. .... 73/35.04 |
| 5,511,422 A | | 4/1996 | Hernandez |
| 5,515,720 A | | 5/1996 | Remboski, Jr. et al. ....... 73/116 |
| 5,614,676 A | * | 3/1997 | Dutt et al. .................... 73/660 |
| 5,616,834 A | | 4/1997 | Lynch et al. .................. 73/116 |
| 5,679,900 A | * | 10/1997 | Smulders ..................... 73/659 |

(List continued on next page.)

OTHER PUBLICATIONS

Molitor et al., "Acoustic roller bearing diagnosis in a closed-loop quality control system", Jun. 4–6, 1996, IEEE, Instrumentation and Measurement Technology Conference, 1996, vol. 1, pp. 654–657.*
Broch, J. "Mechanical Vibration and Shock Measurements." 2. ed—Dinamarca. Bruel & Kjaer Apr. 1984, pp. 152–155.
Textbook, Chapter 4, "Digital Filters", Analog Devices, Inc. 1990, pp. 173–197, no month.

*Primary Examiner*—Hal D Wachsman
(74) *Attorney, Agent, or Firm*—Thomas V. Miller; Brian M. Mancini (57) ABSTRACT

A fault detection method for determining whether a fault exists with a rotating element of a vehicle that includes a transduce, a diagnosis sampler, and a controller. The transducer converts sounds to an electrical signal that includes a noise component generated from the rotating element. The diagnosis sampler provides a sample of the electrical signal to the controller, which has functional aspects such as an envelope detect, a spectrum analysis, and a fault detect. The envelope detect detects an envelope of the electrical signal. The spectrum analysis forms a spectra from the envelope of the electrical signal, where the spectra is associated with the noise component generated from the rotating element. The fault detect determines (from the formed spectra) whether the fault exists with the rotating element.

9 Claims, 5 Drawing Sheets

U.S. PATENT DOCUMENTS

| | | | |
|---|---|---|---|
| 5,841,025 A | 11/1998 | Remboski et al. | 73/117.3 |
| 6,234,021 B1 | 5/2001 | Piety et al. | 73/592 |
| 6,321,602 B1 | 11/2001 | Ben-Romdhane | |
| 6,330,499 B1 * | 12/2001 | Chou et al. | 701/33 |
| 6,370,957 B1 | 4/2002 | Filippenko et al. | |
| 2002/0173889 A1 * | 11/2002 | Odinak et al. | 701/36 |
| 2003/0009270 A1 * | 1/2003 | Breed | 701/29 |
| 2003/0020603 A1 * | 1/2003 | DeLine et al. | 340/425.5 |
| 2003/0061049 A1 * | 3/2003 | Erten | 704/260 |
| 2003/0088346 A1 * | 5/2003 | Calkins et al. | 701/29 |
| 2003/0106375 A1 * | 6/2003 | Sabini et al. | 73/593 |
| 2003/0236672 A1 * | 12/2003 | Aaron et al. | 704/277 |

* cited by examiner

FAULT DETECTION SYSTEM HAVING AUDIO ANALYSIS AND METHOD OF USING THE SAME

The present application claims priority from provisional application, Serial No. 60/373,156, entitled "Fault Detection System Having Audio Analysis and Method of Using the Same," filed Apr. 17, 2002, which is commonly owned and incorporated herein by reference in its entirety. Moreover, this patent application is related to commonly assigned patent U.S. Pat. No. 6,668,220, entitled "Synchronous Sampling of Rotating Elements in a Fault Detection System Having Audio Analysis and Method of Using the Same," filed concurrently herewith and incorporated herein by reference in its entirety.

FIELD OF THE INVENTION

This invention in general relates to the detection of faults in a vehicle and, more particularly, to a fault detection system having audio analysis and a method of using the same.

BACKGROUND OF THE INVENTION

A user of a vehicle may hear an unpleasant sound or feel a strange vibration while operating a vehicle. Most users of vehicles are not trained to know or recognize the source of such a sound or vibration and in many cases significant changes over longer periods of time are so subtle they go undetected. Many unpleasant sounds and strange vibrations are generated by faults of rotating elements in a vehicle such as the tires, the engine, the driveline, and the fan or blower of a the heating, ventilation, and air-conditioning (HVAC) system. Accordingly, there is also a need for aiding the user of a vehicle to identify the source of unpleasant sounds or strange vibrations in the vehicle.

Various systems have been employed for detecting faults on a vehicle. Existing systems require dedicated sensors outside the cabin of a vehicle for each component on the vehicle. These sensors are susceptible to fault over time due to exposure to corrosive and other harsh environments.

In the past, systems have considered using an audio transducer located in close proximity to a component susceptible to a fault. Such systems, however, require multiple audio transducers if there is a desire to monitor multiple components. Additionally, these audio transducers are susceptive to interference from sounds and vibrations of other components. Furthermore, the sensors themselves may be susceptible to corrosion and other faults if they are located in harsh environments.

Accordingly, further improvements are needed to known systems for the monitoring of multiple components on a vehicle. It is, therefore, desirable to provide an improved procedure for detecting faults of rotating elements in a vehicle to overcome most, if not all, of the preceding problems.

While the invention is susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the appended claims.

DETAILED DESCRIPTION

What is described is an improved system and procedure for detecting faults associated with rotating elements on a vehicle. To this end, in one embodiment there is a fault detection system for determining whether a fault exists with a rotating element of a vehicle. The system includes a transducer, a diagnosis ampler, and a controller. The transducer may be a microphone located in the vehicle or converting (step 400 of FIG. 4) sounds to an electrical signal. The electrical signal includes a noise component generated from the rotating element. The diagnosis sampler is connected to the transducer and provides a sample of the electrical signal from the transducer to the controller. The controller has functional aspects such as an envelope detect, a spectrum analysis, and a fault detect. The envelope detect detects an envelope of the electrical signal. The spectrum analysis forms a spectra from th envelope of the electrical signal, where the spectra is associated with the noise component generated from the rotating element. The fault detect determines (from the formed spectra) whether the fault exists with the rotating element.

The controller may also include further functionality, or example, the controller may include a synchronous resample function that synchronizes the envelope of the electrical signal with data from a sensor associated with the rotating element. This step would be performed prior to the formation of the spectra. The synchronous resample function aids in the analysis of vehicle cabin noise. Most rotating elements in a vehicle vary in speed during the operation of the vehicle. If samples are taken at regular time intervals (regardless of vehicle operation), th time sampled spectrum will change as the rotational speed of the element changes. Synchronizing the envelope with data obtained from a sensor of the rotating element solves the problem of varying rotational speeds during operation.

Figure 4:
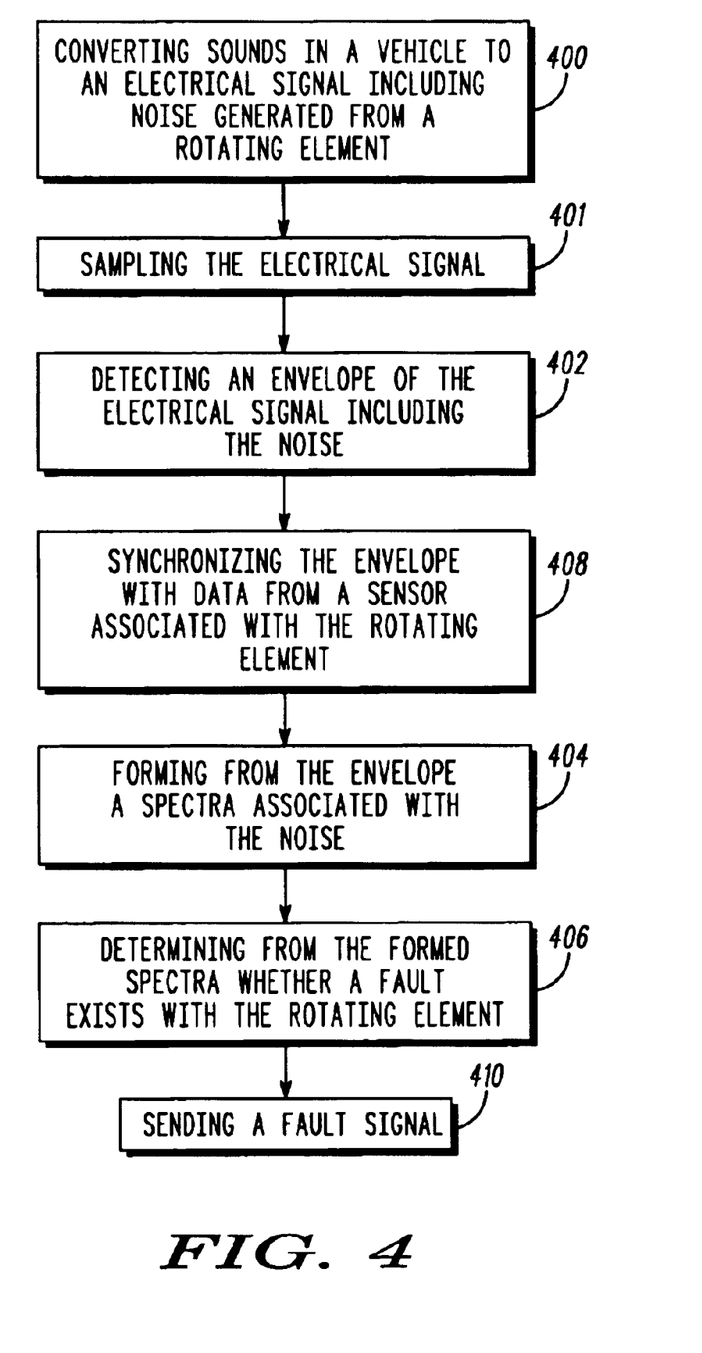
FIG. 4 is a method of fault detection in accordance wit the present invention.

Referring to FIG. 4, another embodiment of the present invention is a method for detecting a fault associated with a rotating element in a vehicle. The steps of the method include: converting (400) sounds within a cabin of a vehicle to an electrical signal where the electrical signal comprises a noise component generated from the rotating element; sampling (401) an electrical signal where the electrical signal comprises a noise component generated from the rotating element; detecting (402) an envelope of the electrical signal where the envelope comprises the noise component generated from the rotating element; forming (404) a spectra from the envelope where the spectra is associated with the noise component generated from the rotating element; and determining (406) (from the formed spectra) whether a fault exists with the rotating element.

A further embodiment of the present invention includes a method for detecting a fault associated with a plurality of rotating elements in a vehicle. The steps of this method include: sampling an electrical signal from a transducer in the vehicle where the electrical signal comprises a plurality of noise components generated from the rotating elements;

detecting an envelope of the electrical signal where the envelope comprises the noise components generated from the rotating elements; forming a plurality of spectra from the envelope where each spectra is associated with one of the noise components generated from the rotating elements; and determining (from each of the plurality of formed spectra) whether a fault exists with one of the rotating elements.

Figure 1:
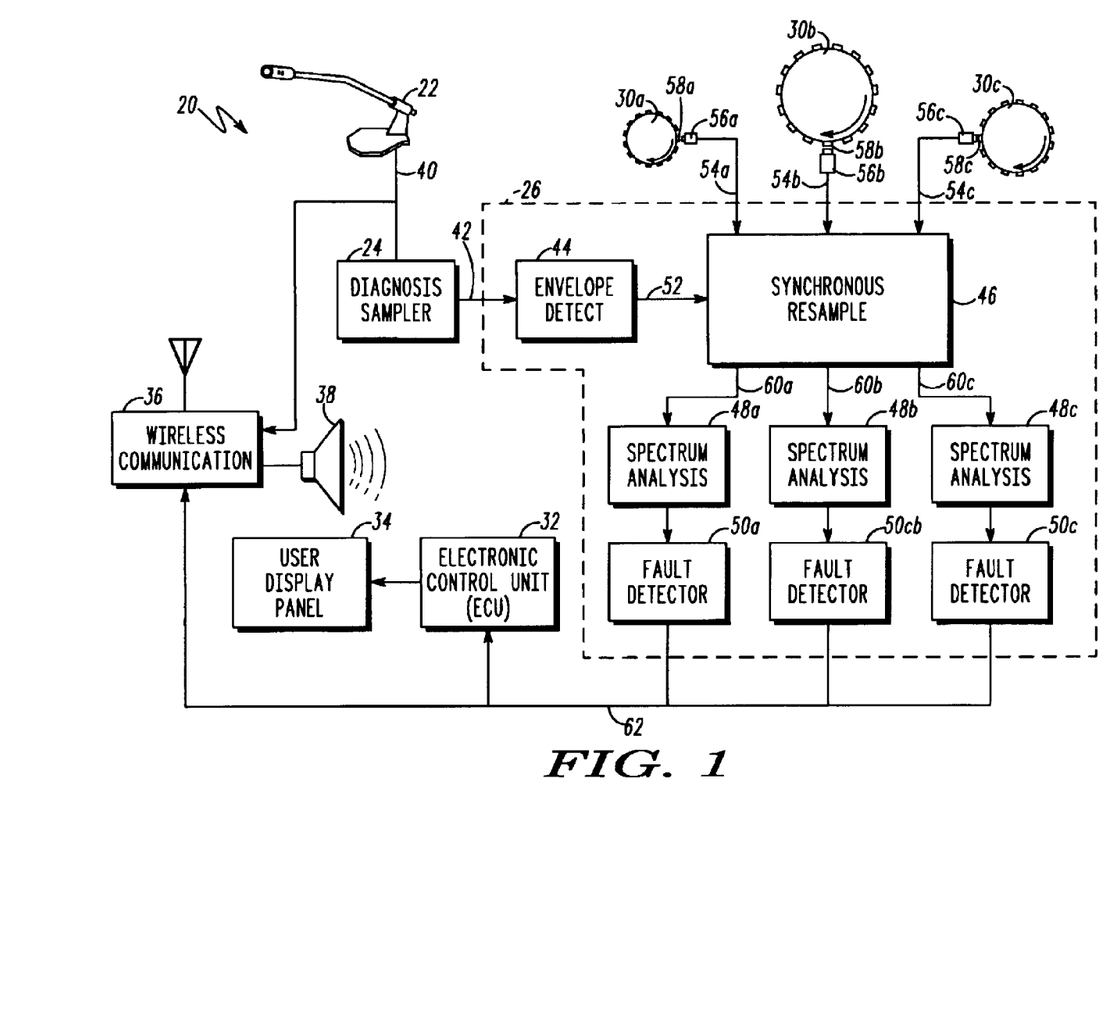
FIG. 1 is a block diagram of a fault detection system according to one embodiment of the present invention.

Now, turning to the drawings, an example use of a fault detection system for a vehicle will be explained. As will be explained in more detail below, the fault detection system samples the sound in a cabin of the vehicle and uses the sampled sound as a diagnostic tool for determining whether a fault exists with rotating elements in the vehicle. Referring to FIG. 1, in one embodiment, a fault detection system 20 generally has a transducer 22, a diagnosis sampler 24, and a controller 26. The fault detection system 20 determines whether a fault or problem exists with one of a plurality of rotating elements 30a, 30b, 30c in the vehicle. Examples of rotating elements 30a, 30b, 30c in the vehicle include elements such as the tires, the engine, the driveline, and the fans or blower for the heating, ventilation, and air-conditioning (HVAC) system.

As discussed in more detail below, after analysis of the sampled sound, a signal representing a fault or problem may be transmitted by the controller 26 to an electronic control unit (ECU) 32. The ECU 32 may then notify the user of the vehicle via a user display panel 34 that a fault or problem exists with a rotating element 30a, 30b, 30c. Alternatively, or additionally, a digital signal representing the fault or problem may be transmitted via a wireless communication device 36 to a service center (shown in FIG. 3).

The transducer 22 may be a microphone located in the cabin of the vehicle. In one embodiment, the transducer 22 is a microphone used for hands-free voice calls through the wireless communication device 36. The wireless communication device 36 is connected to the transducer 22 and to an audio speaker 38 within the cabin. The transducer 22 may also be a microphone used for communication with a remote service center for information and roadside assistance. Utilizing an existing microphone in the cabin provides the advantage of multi-tasking a single component in the vehicle. Alternatively, a separate dedicated transducer 22 may be installed in the vehicle.

The transducer 22 converts sounds in the cabin of the vehicle to an electrical signal 40. In one embodiment, the electrical signal 40 from the transducer 22 is an analog signal. The diagnosis sampler 24 receives the electrical signal 40 from the transducer 22. The purpose of the diagnosis sampler 24 is to sample the electrical signal 40 from the transducer 22 for input to the controller 26. The diagnosis sampler 24 may be a separate integrated circuit from the controller 26. Alternatively, the diagnosis sampler 24 may reside within the controller 26 and be an integral part of the input. The diagnosis sampler 24 allows the electrical signal 40 to be further analyzed by the controller 26.

In one embodiment, the diagnosis sampler 24 takes samples of the electrical signal 40 and converts the electrical signal 40 to a format acceptable to the controller 26. For example, if the controller 26 is a digital signal processor (DSP) controller, the electrical signal 40 is converted to a digital signal 42. Accordingly, the diagnosis sampler 24 may include components such as an amplifier and an Analog to Digital (A/D) converter. The sampling rate should depend on the frequency limit of the transducer 22. For example, in one embodiment, the sampling process would be at least double the highest frequency range of the transducer. This means that for a transducer 22 that can pick up sounds up to 6 kHz, the minimum sampling rate for the diagnosis sampler 24 is 12,000 samples per second. In most embodiments, the diagnosis sampler 24 should be about 16,000 samples per second and having a 12 bit resolution for each sample.

The diagnosis sampler 24 may be configured a number of different ways to sample the electrical signal 40 from the transducer 22. In one embodiment, the diagnosis sampler 24 is configured to continuously sample the electrical signal 40 at select time intervals during the operation of the vehicle. In another embodiment, the diagnosis sampler 24 is configured to sample the electrical signal 40 in response to an instruction from the electronic control unit 32 or controller 26. The instruction to sample the cabin sound could be sent when certain known conditions exist within the vehicle (i.e. when a rotating element is rotating at a certain rate). Furthermore, the diagnosis sampler 24 may be configured to sample the electrical signal 40 or be otherwise activated in response to an instruction from a service center (not shown) and/or the user of the vehicle.

The electrical signal 40 generated by the transducer 22 is a composite of sound components in the cabin of the vehicle. In one embodiment, the digital signal 42 generated by the diagnosis sampler 24 will also be a composite of sound components in the cabin of the vehicle.

One component of the sampled sound will be noise from rotating elements 30a, 30b, 30c of the vehicle. In some cases, the noise related to the actual rotation of rotating elements 30a, 30b, 30c will be much lower in frequency than the limits of the transducer 22. For instance, if the transducer 22 is a microphone for hands-free voice calls or information/road-side assistance services, these microphones can only pick up sounds between the range of 400 Hz and 6 kHz. Accordingly, the transducer 22 may not directly pick up the noise related to the actual rotation of these rotating elements 30a, 30b, 30c if they are below 400 Hz. The noise associated with the rotation of a rotating element 30a, 30b, 30c, however, will propagate to the structure of the vehicle (such as the chassis). Noise through the structure of the vehicle rings in response to forces generated by the rotating elements 30a, 30b, 30c. It has been discovered that the ringing allows a transducer 22 with limited frequency response to detect the state of the rotating elements 30a, 30b, 30c even when the elements themselves are rotating slowly relative to the pass band of the audio system.

For example, as mentioned above, one of the rotating elements 30a, 30b, 30c on a vehicle may be the tires. A tire having a radius of 18 inches will rotate at 560 RPM at 60 MPH. This will cause a repetition rate of 9.3 Hz. Sounds at this frequency are too low for the microphone to pick up much less an audible frequency for a human ear (20 Hz–20 kHz). The tire assembly, however, is attached to the chassis of the vehicle. A 9.3 Hz frequency will generate a vibration to the chassis of the vehicle that will result in a higher frequency noise. The transducer 22 will pick up the higher frequency noise from the chassis caused by the rotating elements.

The vibration noise from the chassis is a composite of several other vibration noises caused from other sources of the vehicle. One aspect of the present invention is directed to associating a noise with a particular rotating element 30a, 30b, 30c from the composite of vibration noises and analyzing that noise to determine a fault or problem for the rotating element 30a, 30b, 30c.

The controller 26 processes the digital signal 42 from the diagnosis sampler 24. A suitable controller 26 for the present invention may includes a digital signal processor (DSP) controller or a Motorola MPC 5100. The controller 26 of the present invention preferably includes a number of functional blocks. In one embodiment, the controller has an envelope detect 44, a synchronous resample 46, a plurality of spectrum analyses 48a, 48b, 48c, and a plurality of fault detects 50a, 50b, 50c. These functional blocks may be microcoded signal processing steps that are programmed as operating instructions in the controller 26.

The envelope detect 44 detects an envelope 52 from the digital signal 42 received from the diagnosis sampler 24. The envelope 52 is generated to capture the peak amplitude values of signal bursts and rings. This can be accomplished by rectification of the digital signal 42 and low pass filtering. Both the rectification and the low pass filtering are done digitally. The rectification may be done by taking the absolute value of the digital signal 42. The rectification process may be a mathematical absolute model or other digital representation known to those of ordinary skill in the art.

The rectified data is then applied to the low pass filter. The cutoff frequency used for the low pass filter is implementation specific. The cutoff frequency will typically depend on the size of the rotating element (such as the size of the rotating tire). It has been found, however, that each of the rotating elements in a vehicle come within a range of 5–100 pulses per second. In a cost efficient implementation, a suitable cutoff frequency for the low pass filtering may be selected between 200–400 Hz. Alternatively, separate low pass filtering may be implemented for each of the rotating elements. In any event, as will be discussed further, the monitoring and analysis of the envelope 52 of cabin sounds enables the detection of faults or problems with a particular rotating element in the vehicle.

Within the envelope 52 is a mixture of sounds from the cabin of the vehicle that were picked up by the transducer 22. Some of these sounds may relate to possible problems of the vehicle and some may not relate to problems of the vehicle. The present invention includes a synchronous resample 46 to correlate and synchronize the noise associated with individual rotating elements 30a, 30b, 30c in the vehicle.

It has been discovered that the vibration noise from the chassis or other vehicle structure generated from the rotating elements 30a, 30b, 30c is closely related to the rotation of that element. Accordingly, knowing the rotation of an element 30a, 30b, 30c allows the controller 26 to synchronize the composite envelope 52 for further analysis of a particular rotating element 30a, 30b, 30c.

To this end, the synchronous resample 46 receives sensor data 54a, 54b, 54c relating to each of the rotating elements 30a, 3b, 30c (step 408 of FIG. 4. The sensor data 54a, 54b, 54c is used to synchronize the composite envelope signal 52 for a particular rotating element 30a, 30b, 30c. The sensor data 54a, 54b, 54c is obtained from sensors 56a, 56b, 56c, respectively, located at each of the rotating elements 30a, 30b, 30c.

In one embodiment, the sensor data 54a, 54b, 54c is representative of the angular displacement of the rotating elements 30a, 30b, 30c. There are a number of ways to measure the angular displacement of an element. In one embodiment, the sensors 56a, 56b, 56c measure a passing tooth 58a, 58b, 58c, respectively, on a rotating wheel of the rotating element 30a, 30b, 30c. For example, a sensor may measure a passing tooth on a rotating wheel attached to an engine's crankshaft. As the engine runs, the sensor typically generates a logic level signal that transitions when the sensor senses the tooth and a subsequent space. As the toothed wheel rotates, responsive to the combustion process in the running engine, the angular displacement signal will typically be a rectangular waveform responsive to angular velocity, or engine speed. The practice of using a toothed wheel on a crankshaft and other rotating elements is commonplace in the field of vehicle control. Of course, those skilled in the art will recognize many other, substantially equivalent, means and methods to measure angular displacement.

The sensor data 54a, 54b, 54c is provided to the synchronous resample 46. The sensor data 54a, 54b, 54c is used to synchronize the composite envelope 52 to generate synchronized envelopes 60a, 60b, 60c associated with each rotating element 30a, 30b, 30c. Accordingly, the synchronized envelope 60a relates to rotating element 30a. The synchronized envelope 60b relates to rotating element 30b. The synchronized envelope 60c relates to rotating element 30c. Each synchronized envelope 60a, 60b, 60c is then further analyzed by a separate spectrum analysis functional block 48a, 48b, 48c.

In one embodiment, the resample of the composite envelope 52 includes giving the envelope signal a new scale (sampling period). For example, the composite envelope 52 may have a sampling period of 16,000 samples per second. There is a need to resample this envelope at a different rate depending on the rate of the rotating elements 30a, 30b, 30c. The synchronous resample 46 forms a synchronized envelope 60a, 60b, 60c depending on the rotating rate of the rotating elements from the sensors 56a, 56b, 56c.

The rotating element 30a in one embodiment may be a tire on a vehicle. Associated with the tire is an anti-brake system (ABS) sensor 56a that can generate data that can be used to determine the rotational rate of the tire at a particular time. The ABS sensor 56a will transmit data 54a to the synchronous resample 46. The synchronous resample 46 receives the data 54a from the ABS sensor 56a. The ABS sensor data 54a is then used as the sampling clock to synchronize the composite envelope 52 to generate a tire synchronized envelope 60a for the tire spectrum analysis 48a. The tire spectrum analysis 48a may then use the tire synchronized envelope 60a as described in more detail below.

Moreover, the rotating element 30b may be the engine of the vehicle (such as a V6 engine). Associated with the engine is a crankshaft position sensor 56b that can generate data that can be used to determine the rotational rate of the engine at a particular time. The crankshaft position sensor 56b will transmit data 54b to the synchronous resample 46. The synchronous resample 46 receives the data 54b from the crankshaft position sensor 56b. The crankshaft position sensor data 54b is then used as the sampling clock to synchronize the composite envelope 52 to generate an engine synchronized envelope 60b for the engine spectrum analysis 48b. The engine spectrum analysis 48b may then use the engine synchronized envelope 60b as described in more detail below.

Furthermore, the rotating element 30c may be the driveline of the vehicle. Associated with the driveline is a vehicle speed sensor 56c that can generate data that can be used to determine the rotational rate of the driveline at a particular time. The vehicle speed sensor 56c will transmit data 54c to the synchronous resample 46. The synchronous resample 46 receives the data 54c from the vehicle speed sensor 56c. The vehicle speed sensor data 54c is then used as the sampling clock to synchronize the composite envelope 52 to generate a driveline synchronized envelope 60c for the driveline spectrum analysis 48c. The driveline spectrum analysis 48c may then use the driveline synchronized envelope 60c as described in more detail below.

The present invention is not limited to analysis of the tires, engine and driveline but may include other types of rotating elements such as the fans or blowers in the heating, ventilation and air conditioning system (HVAC).

Additionally, it is noted that the synchronous resample 46 aids in the analysis of vehicle cabin noise when the rotational rates of the rotating elements is changing over time. The frequency spectrum of the cabin sound will show many features related to the rotation of elements on the vehicle. As indicated earlier, rotating elements such as the tires, the engine, the driveline, and the HVAC blower lead to cabin noise. Most of the rotating elements in a vehicle vary in speed during the operation of the vehicle. If samples are taken at regular time intervals (regardless of vehicle operation), the time sampled spectrum will change as the rotational speed of the element changes. Synchronizing the composite envelope 52 with data 54a, 54b, 54c obtained from sensors 56a, 56b, 56c at the rotation elements 30a, 30b, 30c solves the problem of varying rotational speeds during operation.

There is a separate spectrum analysis function 48a, 48b, 48c performed for each rotating element 30a, 30b, 30c on the vehicle. In one embodiment, the spectrum analysis uses DSP based techniques and, in particular, uses the Fast Fourier Transform (FFT). FFT techniques, as applied to digitized data, provides a powerful method of signal analysis by having the ability to recognize weak signals of defined periodicity buried in a composite signal.

In one embodiment, the present invention uses FFTF techniques to generate spectra that is "order" based as shown in FIGS. 2A–2E. The "orders" shown in the figures are defined as a sine wave cycle per revolution. It has been discovered that noise generated from rotating elements comes out at predictable orders. In other words, the amplitude of the noise is particularly predominating at certain cycles per revolution. This aids in determining whether a fault or problem exists with a particular rotating element 30a, 30b, 30c.

Figure 2A:
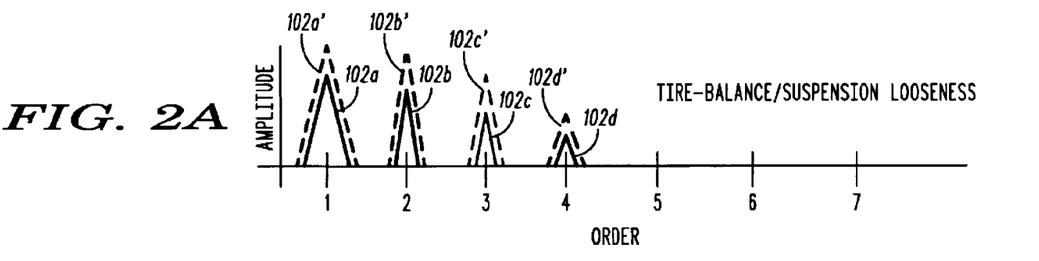
FIGS. 2A–2E are exemplary spectra diagrams for various rotating elements on a vehicle.

For example, if the spectrum analysis 48a is designed to analyze tire faults, the spectrum analysis 48a may generate an "order" based spectra as shown in FIG. 2A. Referring to FIG. 2A, a rotating tire has predictable peak amplitude spikes at orders 1-2-3-4. The peak amplitude decreases as the order increases until the harmonics are insignificant compared to systematic noise. The solid line amplitude spikes 102a–102d refer to amplitude spikes that are consistent with a rotating tire that does not have a fault or problem with balance or suspension looseness. The dashed line amplitude spikes 102a'–102d' refer to amplitude spikes that are consistent with a rotating tire that has a fault or problem with balance or suspension looseness. The amplitude spikes 102a'–102d' associated with a fault or problem are greater than the amplitude spikes 102a–102d associated with normal tire rotation.

Figure 2B:
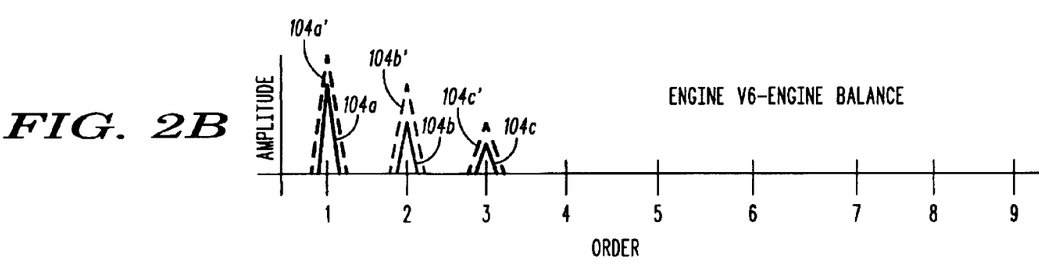
Figure 2C:
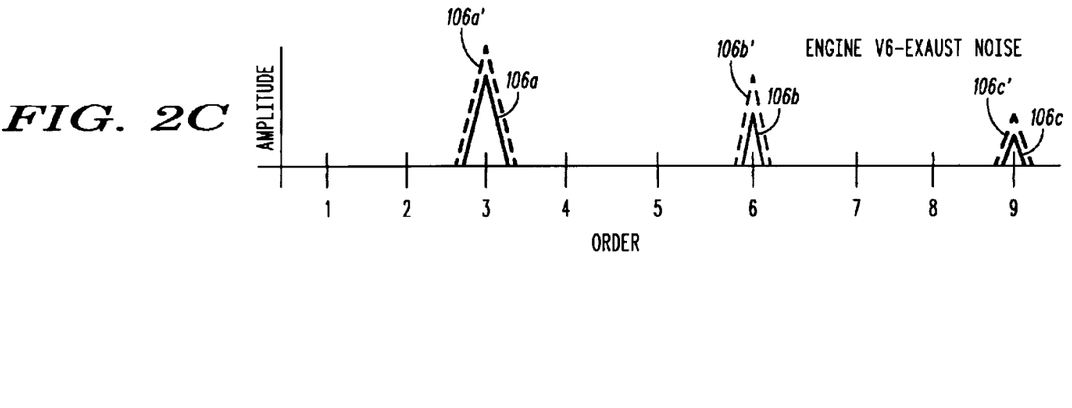

If the spectrum analysis 48b is designed to analyze engine faults (such as a V6 engine), the spectrum analysis 48b may generate an "order" based spectra as shown in FIGS. 2B and 2C. Referring to FIG. 2B, an engine has predictable peak amplitude spikes at orders 1-2-3 when determining whether the engine has a balance problem. The peak amplitude decreases as the order increases until the harmonics are insignificant compared to systematic noise. The solid line amplitude spikes 104a–104c refer to amplitude spikes that are consistent with an engine that does not have a fault or problem with balance. The dashed line amplitude spikes 104a'–104c' refer to amplitude spikes that are consistent with an engine that has a fault or problem associated with engine balance. The amplitude spikes 104a'–104c' associated with a fault or problem are greater than the amplitude spikes 104a–104c associated with normal engine operation.

Referring to FIG. 2C, an engine also has predictable peak amplitude spikes at orders 3-4-9 when determining whether there is exhaust noise (such as a leaky muffler). The peak amplitude decreases as the order increases until the harmonics are insignificant compared to systematic noise. The solid line amplitude spikes 106a–106c refer to amplitude spikes that are consistent with an engine that does not have a fault or problem with exhaust noise. The dashed amplitude spikes 106a'–106c' refer to amplitude spikes that are consistent with an engine that has a fault or problem associated with exhaust noise. The amplitude spikes 106a'–106c' associated with a fault or problem are greater than the amplitude spikes 106a–106c associated with normal engine operation.

Figure 2D:
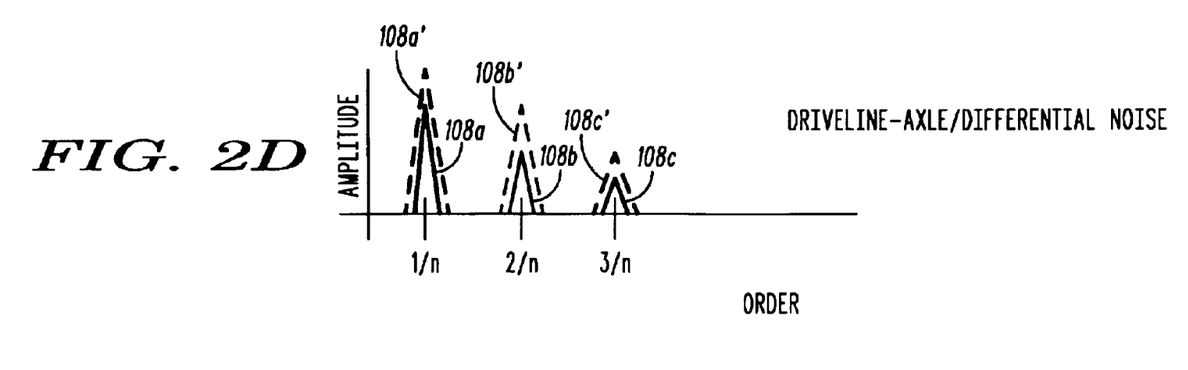
Figure 2E:
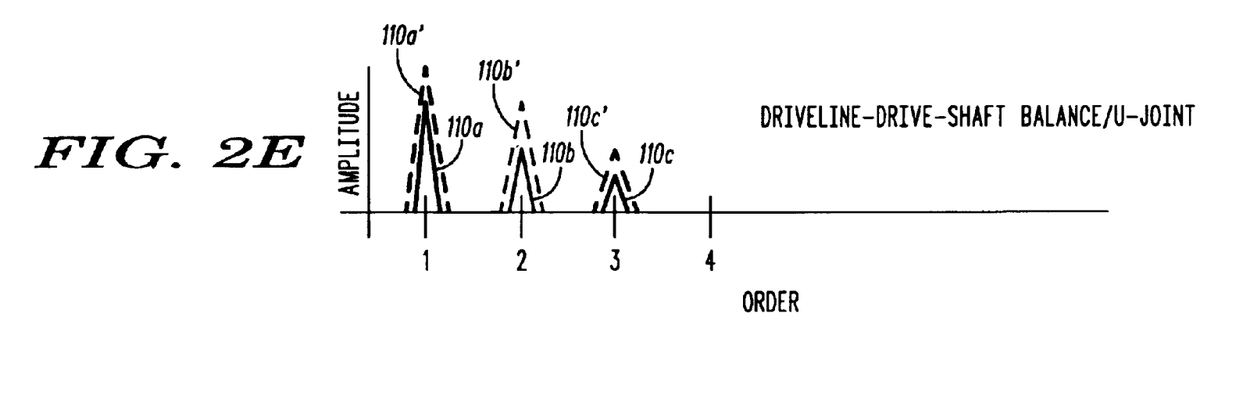

If the spectrum analysis 48c is designed to analyze driveline faults, the spectrum analysis 48c may generate an "order" based spectra as shown in FIGS. 2D and 2E. Referring to FIG. 2D, a driveline has predictable peak amplitude spikes at orders 1/n, 2/n, 3/n, where n is the numerical ratio of the gearing for the rear axle. The peak amplitude decreases as the order increases until the harmonics are insignificant compared to systematic noise. The solid line amplitude spikes 108a–108c refer to amplitude spikes that are consistent with a driveline that does not have a fault or problem with the axle alignment or differential noise. The dashed amplitude spikes 108a'–108c' refer to amplitude spikes that are consistent with a driveline that has a fault or problem associated with axle alignment or differential noise. The amplitude spikes 108a'–108c' associated with a fault or problem are greater than the amplitude spikes 108a–108c associated with normal driveline operation.

Referring to FIG. 2E, a driveline also has a predictable peak amplitude spikes at orders 1-2-3. The peak amplitude decreases as the order increases until the harmonics are insignificant compared to systematic noise. The solid line amplitude spikes 110a–110c refer to amplitude spikes that are consistent with a driveline that does not have a fault or problem with drive-shaft balance or a universal joint. The dashed amplitude spikes 110a'–110c' refer to amplitude spikes that are consistent with a driveline that has a fault or problem associated with the balance of the drive-shaft or the universal joint (such as the universal joint being loose). The amplitude spikes 110a'–110c' associated with a fault or problem are greater than the amplitude spikes 110a–110c associated with normal driveline operation.

Accordingly, the use of the spectrum analysis 48a, 48b, 48c provides the benefit of identifying and analyzing repeating signals. In sum, rotating elements on the vehicle have predictable repeating orders. By analyzing the amplitude spikes associated with these repeating orders, one can determine if a fault has occurred by comparing the current spectra with spectra known to represent a rotating element that is operating properly (without faults).

In one embodiment, the determination of whether a fault or problem exists is accomplished through a series of fault detects 50a, 50b, 50c, associated with each rotating element 30a, 30b, 30c. As indicated above, when analyzing the spectra of a particular rotating element on a vehicle, it has been discovered that a fault or problem can be detected if the peak amplitude is higher than its normal operation. Thus, in one embodiment, a predetermined threshold may be associated with each above-described condition.

The predetermined threshold can be implemented in a number of ways. For example, one embodiment includes an integration method to determine the area of the amplitude spikes for the spectra. A value for the predetermined threshold can be set that is slightly greater than the area of the amplitude spikes that would exist for a rotating element that is operating properly (without faults). In other words, the predetermined threshold should represent an acceptable value of the area of the amplitude spikes before a fault or problem is detected with a particular rotating element. If the area beneath the amplitude spikes (under analysis) is greater than the predetermined threshold, a fault exists with the rotating element. If the area beneath the amplitude spikes (under analysis) is less than the predetermined threshold, no fault exists with the rotating element.

In another embodiment, the predetermined threshold represents an acceptable maximum height for the amplitude spikes within the spectra. Here, the predetermined threshold is a maximum height (or value) slightly greater than a height of an amplitude spike that would exist for a rotating element that is operating properly (without faults). When the amplitude spikes (under analysis) are greater than the predetermined threshold, a fault exists with the rotating element. In either embodiment, a different predetermined threshold would need to be determined for each type of rotating element and for each type of problem that may possibly exist for that rotating element. The predetermined thresholds may be installed by the manufacturer and based on the type and design of the vehicle. The predetermined thresholds may also be determined from historical data on a fleet of vehicles of the same make and model of vehicle.

In sum, when the amplitude spikes are at or below a predetermined threshold, the vehicle is determined to have no faults or problems. However, when the amplitude spikes are above the predetermined threshold, the vehicle is determined to have a fault or problem.

It is noted that the predetermined thresholds described herein may vary based on the speed of the rotating element. Accordingly, in one implementation of the present invention, each fault detect 50a, 50b, 50c contains a look-up table that can be indexed by the current rotational speed of the rotating element 30a, 30b, 30c. For this implementation, the fault detects 50a, 50b, 50c need to have access to the data received by the controller 26 from sensors 56a, 56b, 56c.

In another implementation, the fault detects 50a, 50b, 50c include historical averages of acceptable amplitude spikes for a particular rotating element. For example, if the diagnosis sampler 24 is sampling the vehicle cabin at regular intervals during operation, a historical threshold average can be developed for each rotating element. In this embodiment, the controller 26 stores in memory the amplitude spikes for different rotational speeds of the rotating elements 30a, 30b, 30c to develop the historical threshold average. After an acceptable historical threshold average has been compiled, the fault detects 50a, 50b, 50c would then compare the existing amplitude spikes at a specific time to the historical threshold average at the existing rotational speed. If there was a sharp contrast between the existing amplitude spikes and the historical threshold average, then a fault or problem would be detected by the controller 26.

If a fault or problem is determined by the controller 26, a fault signal 62 may be provided to the user of the vehicle. In one embodiment, the fault signal 62 is provided (step 410 of FIG. 4) to the electronic control unit (ECU) 32 of the vehicle. In this embodiment, the ECU 32 is connected to a user display panel that notifies the user of the vehicle that a fault or problem exists with a particular rotating element 30a, 30b, 30c.

Figure 3:
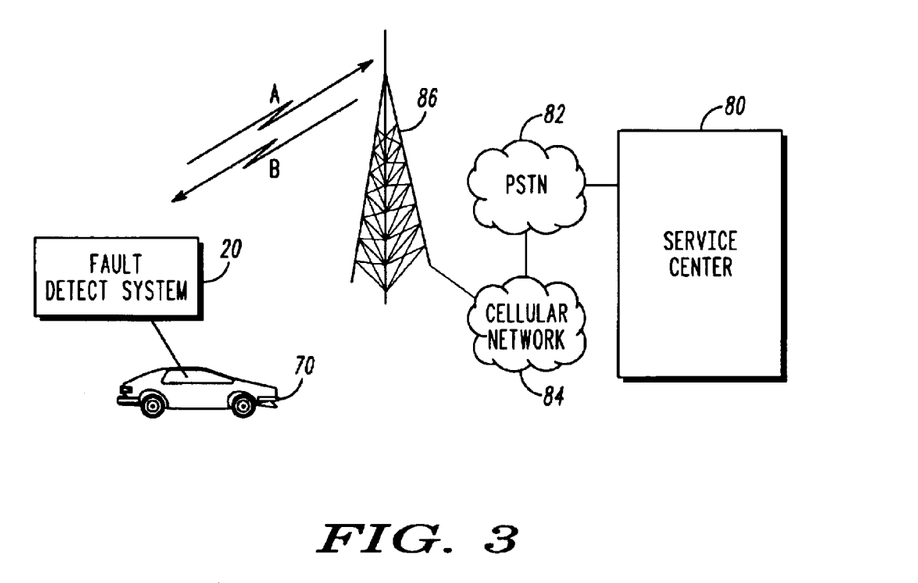
FIG. 3 is a block diagram of another embodiment of a system incorporating the fault detection system of the present invention.

In another embodiment of the present invention, as shown in FIG. 3, the fault detection system 20 is used in connection with a Telematics system. The Telematics system includes a fault detection system 20 (within a vehicle 70) and a service center 80.

The fault detection system 20 and the service center 80 may communicate with each other via wireless communication. The wireless communications are illustrated in FIG. 3 by communication arrows A and B. Communication arrow A may represent a communication by the user of the vehicle 70 asking e service center 80 for help in analyzing a problem with the vehicle 70. Communication arrow A may also represent a communication by the fault detection system 20 (step 410 of FIG. 4). This communication could be a fault signal 62 generated by the controller 26. Alternatively, the controller 26 may directly send the synchronized envelopes 60a, 60b, 60c or raw spectra data direct to the service center 80. The service center 80 would then perform the fault detect functions. The advantage of this approach is that it allows the flexibility of changing the predetermined thresholds based on historical data from fleet studies on vehicles with the same make and model. 80 for help in analyzing a problem with the vehicle 70. Communication arrow A may also represent a communication by the fault detection system 20. This communication could be a fault signal 62 generated by the controller 26. Alternatively, the controller 26 may directly send the synchronized envelopes 60a, 60b, 60c or raw spectra data directly to the service center 80. The service center 80 would then perform the fault detect functions. The advantage of this approach is that it allows flexibility of changing the predetermined thresholds based on historical data from fleet studies on vehicles with the same make and model.

Communication arrow B may represent a communication by the service center 80 instructing or informing the user of the vehicle 70 of the type of fault or problem that may appear to exist with the vehicle 70. In a further embodiment, the diagnosis sampler 24 may be configured to take a sample of the audio within the cabin of the vehicle on demand by the service center 80 through communication arrow B.

As shown in FIG. 3, in one embodiment, the communications A and B may be a cellular wireless communication that is sent through the public switched telephone network (PSTN) 82, a cellular network 84, and a base station antenna 86. Those of ordinary skill in the art, having the benefit of this disclosure, will appreciate that many possible wireless communication methods may be used for communications between the vehicle 70 and e service center 80. In one embodiment, the communications are via a cellular wireless communication systems such as Advanced Mobile Phone Service (AMPS), Code Division Multiple Access (CDMA), Global System for Mobile (GSM) communication or Time Division Multiple Access (TDMA). The transmission between the vehicle 70 and the service center 80 may also be made by other wireless communications such as satellite communications.

Having the fault detection system 20 wirelessly connected to a service center 80 has several benefits as will be apparent from the following description. The user of a vehicle 70 having the fault detection system 20 may hear a noise or believes that the vehicle 70 is not responding properly. The user of the vehicle 70 may push a button in the vehicle 70 to establish a wireless communication with the service center 80. The service center 80 receives the fault signals 62 from the vehicle 70 via the wireless communication device 36 (as shown in FIG. 1). The service center 80 may then look at the fault signals 62. If there is a fault or problem, the service center 80 may inform the user of the vehicle 70 of the apparent problem. For example, it may appear from the fault signals 62 that there is a severe misalignment problem with the axle. The service center 80 may then instruct the user of the vehicle that the vehicle should be taken (or even towed) to a car facility immediately. Alternatively, it may appear from the fault signals 62 that there is a problem with the HVAC fan or blower. The service center 80 may then inform the user of the vehicle 70 that the problem does not appear to be serious but instruct the user to turn off the air conditioning.

The above description of the present invention is intended to be exemplary only and is not intended to limit the scope of any patent issuing from this application. The present invention is intended to be limited only by the scope and spirit of the following claims.

What is claimed is:

1. A method for detecting a fault associated with a rotating element in a vehicle, the method comprising the steps of:

converting sounds within a cabin of the vehicle to an electrical signal, the electrical signal including a noise component generated from the rotating element;

sampling the electrical signal;

detecting an envelope of the electrical signal, the envelope including the noise components generated from the rotating element;

synchronizing the envelope with data from a sensor associated with the rotating element;

forming a spectra from envelope, the spectra being associated with the noise components generated from the rotating elements; and determining from the formed spectra whether the fault exists with the rotating element by comparing an amplitude of the formed spectra over a plurality of orders with a predetermined threshold for each order, wherein the predetermined threshold is different for different rotational speeds of the rotating element.

2. The method of claim 1, wherein the converting step includes a microphone within a cabin of the vehicle for converting the sounds.

3. The method of claim 1, wherein the step of synchronizing includes correlating the sensor data with the electrical signal to form a composite envelope for the rotating element, and the step of forming the spectra from the envelope includes forming a spectra of the synchronized composite envelope.

4. The method of claim 3, wherein the synchronizing step includes using the sensor data of the rotating element as a sampling clock to synchronize the composite envelope for that rotating element.

5. The method of claim 1 comprising the further step of sending a fault signal to at least one of an electronic control unit of the vehicle when it is determined that a fault exists with the rotating element or sending fault data to a remote service center to perform fault detection.

6. A method for detecting whether a plurality of fault exist with a plurality of rotating elements in a vehicle, the method comprising the steps of:

converting sounds within a cabin of the vehicle to an electrical signal, the electrical signal including noise components generated from the plurality of rotating elements;

sampling the electrical signal;

detecting an envelope of the electrical signal, the envelope including the noise components generated from the rotating elements;

synchronizing the envelope with data from a sensor associated with each of the plurality of rotating elements by correlating the sensor data with the electrical signal by using the sensor data of one rotating element as a sampling clock to form a synchronized composite envelope for each of the plurality of rotating element;

forming a plurality of spectra of the synchronized composite envelopes, each spectra being associated with one of the noise components generated from the plurality of rotating elements; and determined from each of the plurality of formed spectra whether one of the faults exist with one of the plurality of rotating elements.

7. The method of claim 6, wherein the converting step includes a microphone within a cabin of the vehicle also used for converting the sounds.

8. The method of claim 6, wherein the step of determining whether one of the faults exist includes a comparison between an amplitude of the formed spectra over a plurality of orders and predetermined threshold for each order, wherein the predetermined threshold is different for different rotational speeds of the plurality of rotating elements.

9. The method of claim 6, comprising the further step of sending a fault signal to at least one of an electrical control unit of the vehicle when it is determined that one of the faults exist with one of the plurality of rotating elements or sending fault data to a remote service center to perform fault detection.

* * * * *